United States Patent [19]

Perry

[11] 4,181,022
[45] Jan. 1, 1980

[54] PRESSURE RISE TUBE SAMPLER

[76] Inventor: Jack A. Perry, 920 Mohawk St., Apt. #344, Bldg. #6, Lewiston, N.Y. 14092

[21] Appl. No.: 970,213

[22] Filed: Dec. 18, 1978

[51] Int. Cl.² .............................................. G01N 1/10
[52] U.S. Cl. ................................................. 73/422 TC
[58] Field of Search .......... 73/422 TC, 422 R, 421 B, 73/421 R

[56] References Cited

U.S. PATENT DOCUMENTS

| | | | |
|---|---|---|---|
| 2,713,268 | 7/1955 | Langsenkamp | 73/421 B |
| 3,200,649 | 8/1965 | Peterson | 73/422 TC |
| 3,811,324 | 5/1974 | Doncer | 73/421 B |
| 3,812,722 | 5/1974 | Soudelier | 73/422 TC |
| 4,024,766 | 5/1977 | Perry | 73/422 R |

FOREIGN PATENT DOCUMENTS 1270530  4/1972  United Kingdom .................. 73/421 B

*Primary Examiner*—S. Clement Swisher
*Assistant Examiner*—Denis E. Corr
*Attorney, Agent, or Firm*—Joseph P. Gastel

[57] ABSTRACT

A pressure rise tube sampler for sampling liquid flowing in a conduit under high pressure including a pressure rise tube, a side arm sampler in communication with the rise tube, a first valve arrangement for permitting high pressure liquid to enter the rise tube from a high pressure liquid conduit, a liquid level control for closing the first valve arrangement after the liquid level in the rise tube has exceeded the level of the side arm and for opening a second valve arrangement to permit the liquid to be forced from the rise tube by the air which it compressed in entering the rise tube, and a third valve arrangement in the side arm for permitting liquid to be discharged therefrom into a container for analysis purposes.

3 Claims, 3 Drawing Figures

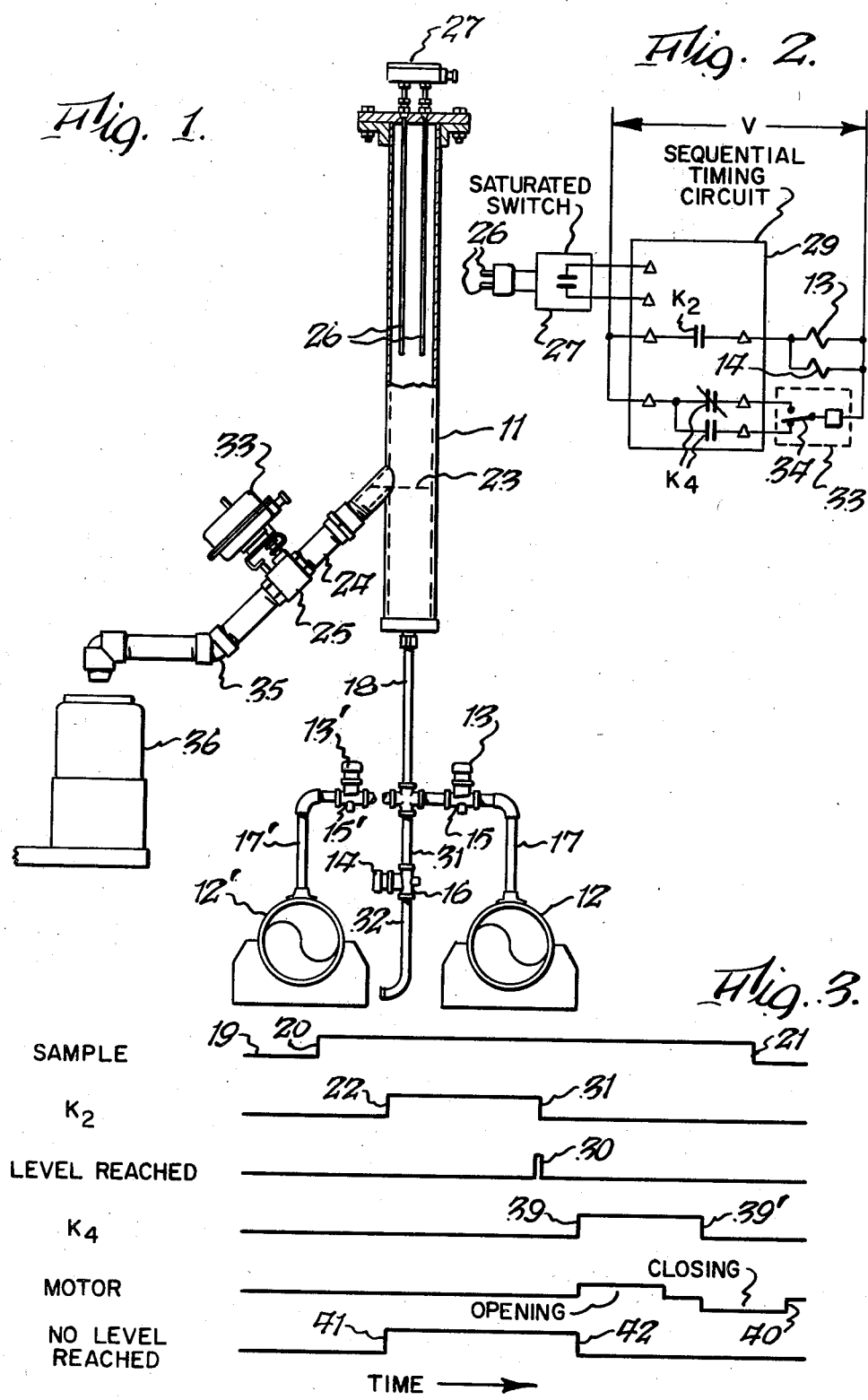

PRESSURE RISE TUBE SAMPLER

BACKGROUND OF THE INVENTION

The present invention relates to an improved sampling device which provides a measured sample of liquid.

By way of background, liquid samplers are used in industry for the purpose of obtaining samples of waste water or other liquids for analysis. One system is disclosed in U.S. Pat. No. 4,024,766 which utilizes vacuum to cause liquid to rise into a rise tube from which it fills a side arm with a measured amount of liquid and thereafter pressurized air is used to clear the rise tube, while the side arm retains a measured amount of liquid. Systems of the foregoing type require a vacuum-pressure pump for creating the vacuum required to draw liquid into the rise tube and thereafter creating the pressure to expel it.

SUMMARY OF THE INVENTION

In certain liquid conveying systems, including fresh water conducting systems, chemical process systems, sewage systems and waste water systems, the liquid is conveyed through conduits at high pressures. The improved pressure rise tube sampler of the present invention utilizes the pressure of the liquid itself for obtaining a sample, thereby obviating the need for a vacuum-pressure pump.

It is therefore the object of the present invention to provide an improved liquid sampling system which utilizes the pressure of liquid to be sampled as the source of energy for filling a side arm associated with a rise tube, for the ultimate purpose of obtaining a measured amount of liquid. Other objects and attendant advantages of the present invention will readily be perceived hereafter.

The present invention relates to a pressure rise tube sampler for liquid comprising first conduit means in communication with a high pressure liquid line, a rise tube coupled to said first conduit means, first valve means for selectively permitting communication between said first conduit means and said rise tube to permit high pressure liquid to enter said rise tube, second conduit means selectively coupled to said rise tube for disposing of liquid from said rise tube, second valve means for selectively permitting communication between said rise tube and said second conduit means, side arm sampler means in communication with said rise tube, first control means for selectively closing said second valve means and opening said first valve means to permit liquid to rise in said rise tube, level sensing means for detecting when liquid has reached a sufficient level in said rise tube to fill said side arm sampler means, second control means coupled to said detecting means for closing said first valve means and opening said second valve means in response to said sensing of said sufficient level by said detecting means to thereby discharge liquid from said rise tube, third valve means in said side arm for selectively permitting discharge of liquid from said side arm, and third control means for opening said third valve means to discharge said liquid therefrom. The various aspects of the present invention will be more fully understood when the following portions of the specification are read in conjunction with the accompanying drawings wherein:

BRIEF DESCRIPTION OF THE DRAWINGS

FIG. 1 is a fragmentary schematic view of the improved pressure rise tube sampler of the present invention;

FIG. 2 is a schematic electrical wiring diagram for the pressure rise tube sampler of FIG. 1; and FIG. 3 is a timing diagram.

DESCRIPTION OF THE PREFERRED EMBODIMENTS

The improved pressure rise tube sampler 10 of the present invention includes a rise tube 11 for receiving liquid from a high pressure liquid line 12 solely as a result of the pressure within the liquid line. This eliminates the necessity for a vacuum source for drawing liquid into rise tube 11, as required in the system shown in U.S. Pat. No. 4,024,766.

Whenever it is desired to obtain a sample of liquid flowing in conduit 12, relay contact $K_2$ is energized in response to a predetermined condition, which may be the expiration of a predetermined period of time or any other condition, as set forth in detail in U.S. Pat. No. 4,024,766. The initiation of a sample cycle is indicated by time 20 on time line 19 in FIG. 3, and the sample cycle will last until line 21. At time 22, the energization of relay contacts $K_2$ will complete an electrical circuit through solenoids 13 and 14 to open normally closed valve 15 and close normally open valve 16, respectively. Upon the opening of valve 15 high pressure liquid from conduit 12 will pass through conduit 17, valve 15, and conduit 18 into pressure rise tube 11. The liquid will rise in tube 11 until level 23 is reached, and further rising of the liquid will cause it to enter side arm conduit 24 and fill it to level 23. At this point liquid cannot flow out of side arm conduit 24 because valve 25 is closed. As liquid continues to rise in tube 11, a point will be reached where the liquid reaches conductive level probes 26. This will cause saturated switch 27 to close and provide a "level reached signal" 30 to sequential timing circuit 29. This will cause relay contact $K_2$ to return to a normally open condition to disrupt the flow of current to solenoids 13 and 14 at time 31, whereupon valve 15 will return to its normally closed position and valve 16 will return to its normally open position. When the latter occurs, the liquid in tube 11 will therefore flow downwardly through conduit 18, conduit 31, valve 16 and conduit 32 to a discharge area or sump. The flow of liquid from rise tube 11 will be aided by the fact that the air above the liquid level in rise tube 11 was compressed during the filling of the rise tube.

It is to be noted that the liquid to the level 23 is retained in side arm conduit 24 for a short period of time after liquid has been discharged from rise tube 11. The normally open relay contacts $K_4$ are then closed at time 39 after a predetermined time delay after the opening of valve 16. This will complete a circuit to motor 33 which drives valve 25 between open and closed positions. The energization of motor 33 through now closed contacts $K_4$ and normally closed switch 34 will cause motor 33 to open sample discharge valve 25 so that the liquid previously trapped in side arm 24 will flow through valve 25 and conduit 35 to sample receiving container 36. The continued rotation of motor 33 will cause switch arm 34 to move to its other position than the one shown in the drawing. At time 39' the normally closed contacts $K_4$ will close to complete a circuit to motor 33 to cause it to continue to rotate until switch arm 34 returns to the position shown in FIG. 2 at time 40, whereupon the motor 33 will stop with valve 25 in closed position.

The circuit will remain in the condition wherein solenoid valve 15 is closed and solenoid valve 16 is open and valve 25 is closed, until such time that another sample is desired, at which time the foregoing sequence will be repeated.

The circuit includes a no-level reached portion (not shown) which is energized at time 41. If no sample is taken by time 42, a "fault" signal is energized. This portion of the circuit is similar to that described in U.S. Pat. No. 4,024,766. In fact, the entire circuit operates in an analogous manner, the only difference being in that the sample is obtained by pressure of the system rather than by creating a vacuum.

As can be seen from the drawings, the sampler of the present invention can be used to sample liquid flowing in a plurality of conduits. Thus, for example, conduit 12' may be placed in communication with conduit 18 through conduit 17' and solenoid operated valve 15' which operates in the same way as valve 15. In short, it can be seen that any number of high pressure conduits, such as 12 and 12', may be selectively placed in communication with conduit 18 through solenoid operated valves, such as 13 and 13', in order to obtain samples.

As a further modification, if desired, a pressure relief valve can be located in rise tube 11 to prevent compression of the air therein beyond a predetermined value.

It can thus be seen that the improved sampling system of the present invention, which produces a sample by using the pressure of the liquid being sampled, is manifestly capable of achieving the above-enumerated objects, and while preferred embodiments have been disclosed, it will be appreciated that the present invention is not limited thereto but may be otherwise embodied witin the scope of the following claims.

What is claimed is:

1. A pressure rise tube sampler for liquid comprising first conduit means in communication with a high pressure liquid line, a rise tube coupled to said first conduit means, first valve means for selectively permitting communication between said first conduit means and said rise tube to permit high pressure liquid to enter said rise tube, second conduit means effectively coupled to said rise tube for disposing of liquid from said rise tube, second valve means for selectively permitting communication between said rise tube and said second conduit means, side arm sampler means in communication with said rise tube, first control means for selectively closing said second valve means and opening said first valve means to permit liquid to rise in said rise tube, level sensing means for detecting when liquid has reached a sufficient level in said rise tube to fill said side arm sampler means, second control means coupled to said detecting means for closing said first valve means and opening said second valve means in response to said sensing of said sufficient level by said detecting means to thereby discharge liquid from said rise tube, third valve means in said side arm for selectively permitting discharge of liquid from said side arm, and third control means for opening said third valve means to discharge said liquid therefrom.

2. A pressure rise tube sampler for liquid as set forth in claim 1 wherein said level sensing means comprise probes in said rise tube at an elevation above said side arm.

3. A pressure rise tube sampler for liquid as set forth in claim 1 wherein said first and second valve means are solenoid operated valves.

* * * * *